United States Patent
Yin et al.

(10) Patent No.: US 9,097,642 B2
(45) Date of Patent: Aug. 4, 2015

(54) X-RAY DOSE ESTIMATION TECHNIQUE

(71) Applicant: General Electric Company, Schenectady, NY (US)

(72) Inventors: Zhye Yin, Schenectady, NY (US); Bruno Kristiaan Bernard De Man, Clifton Park, NY (US); Xiaoyu Tian, Durham, NC (US)

(73) Assignee: General Electric Company, Niskayuna, NY (US)

( * ) Notice: Subject to any disclaimer, the term of this patent is extended or adjusted under 35 U.S.C. 154(b) by 250 days.

(21) Appl. No.: 13/649,942

(22) Filed: Oct. 11, 2012

(65) Prior Publication Data

US 2014/0105356 A1 Apr. 17, 2014

(51) Int. Cl.
 *G01N 23/04* (2006.01)
 *A61B 6/00* (2006.01)

(52) U.S. Cl.
 CPC .............. *G01N 23/04* (2013.01); *A61B 6/542* (2013.01)

(58) Field of Classification Search
 USPC .......................................................... 378/95
 See application file for complete search history.

(56) References Cited

U.S. PATENT DOCUMENTS

| | | | |
|---|---|---|---|
| 5,394,452 A * | 2/1995 | Swerdloff et al. | 378/65 |
| 5,844,241 A | 12/1998 | Liu et al. | |
| 5,870,697 A | 2/1999 | Chandler et al. | |
| 6,163,589 A | 12/2000 | Vartanian | |
| 6,345,114 B1 * | 2/2002 | Mackie et al. | 382/132 |
| 7,756,243 B2 | 7/2010 | Gohno | |
| 7,856,082 B2 * | 12/2010 | Flynn et al. | 378/65 |
| 7,929,742 B2 | 4/2011 | Maltz | |
| 7,983,457 B2 | 7/2011 | Toth et al. | |
| 8,306,184 B2 * | 11/2012 | Chang et al. | 378/62 |
| 8,714,818 B2 * | 5/2014 | Tesic et al. | 378/207 |
| 2003/0185343 A1 | 10/2003 | Horiuchi | |
| 2008/0292055 A1 | 11/2008 | Boone | |
| 2012/0150505 A1 | 6/2012 | Couch et al. | |

OTHER PUBLICATIONS

Dixon et al. "Comprehensive Methodology for the Evaluation of Radiation Dose in X-Ray Computed Tomography", AAPM Report No. III; The Future of CT Dosimetry, Feb. 2010, pp. 1-36, American Association of Physicists in Medicine; ISSN:0271-7344.

* cited by examiner

*Primary Examiner* — Phillip A Johnston
(74) *Attorney, Agent, or Firm* — Melissa K. Dobson

(57) ABSTRACT

Embodiments of the disclosure relate to projection-based dose estimation for X-ray systems, such as X-ray imaging systems. For example, in one embodiment, an X-ray system is capable of estimating an X-ray dose based on an intensity profile of the detected X-rays that have passed through a scanned object and an estimated mass of the object. In one embodiment, the intensity profile may be compared to a baseline scan to acquire an estimate of energy interaction with the object.

22 Claims, 11 Drawing Sheets

US 9,097,642 B2

X-RAY DOSE ESTIMATION TECHNIQUE

BACKGROUND

The subject matter disclosed herein relates to X-ray imaging techniques and, more particularly, techniques for estimating a received X-ray dose.

In non-invasive imaging systems, X-ray tubes are used in various X-ray systems and computed tomography (CT) systems as a source of X-ray radiation. The radiation is emitted in response to control signals during an examination or imaging sequence. An emitter within the cathode may emit a stream of electrons in response to heat resulting from an applied electrical current, and/or an electric field resulting from an applied voltage to a properly shaped metallic plate in front of the emitter. The anode may include a target that is impacted by the stream of electrons. The target may, as a result of impact by the electron beam, produce X-ray radiation to be emitted toward an imaged volume. In such imaging systems, a portion of the radiation passes through a subject of interest, such as a patient, baggage, or an article of manufacture, and impacts a digital detector or a photographic plate where the image data is collected. The signals may then be processed to generate an image that may be displayed for review. In other systems, such as systems for oncological radiation treatment, a source of X-rays may be used to direct ionizing radiation toward a target tissue. Regardless of the type of X-ray system used, it may be beneficial to limit X-ray exposure during individual imaging or treatment events. Accordingly, an X-ray device may use settings that achieve appropriate imaging or therapy results at a lowest possible X-ray exposure.

BRIEF DESCRIPTION

In one embodiment, an X-ray system is provided that includes an X-ray source configured to generate an X-ray beam and a detector configured to detect X-rays of the X-ray beam that pass through an object. The X-ray system also includes a processor coupled to the detector and configured to receive information generated by the detector related to the detected X-rays. The processor is configured to execute instructions for: determining an intensity profile of the detected X-rays that pass through the object; determining an attenuation profile of the detected X-rays that pass through the object; estimating an energy interaction with the object based on the intensity profile; estimating a mass of the object based on the attenuation profile; and determining an estimated dose value based at least in part on the energy interaction with the object and the mass of the object.

In another embodiment, a method is provided that uses a processor and that includes that steps of receiving information generated by an X-ray detector related to one or more X-ray images of an object; determining an intensity profile of detected X-rays based on the information; determining an attenuation profile of detected X-rays based on the information; estimating an energy interaction with the object based on the intensity profile; estimating a mass of the object based on the attenuation profile; and determining an estimated dose value based at least in part on the energy interaction with the object and the mass of the object.

In another embodiment, an X-ray system include a processor configured to receive information generated by an X-ray detector related to X-rays that have passed through an object, wherein the processor is configured to execute instructions for: determining an intensity profile of the detected X-rays that pass through the object; estimating an energy interaction with the object based on the intensity profile; and determining an estimated dose value based at least in part on the energy interaction with the object and an estimated mass of the object.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
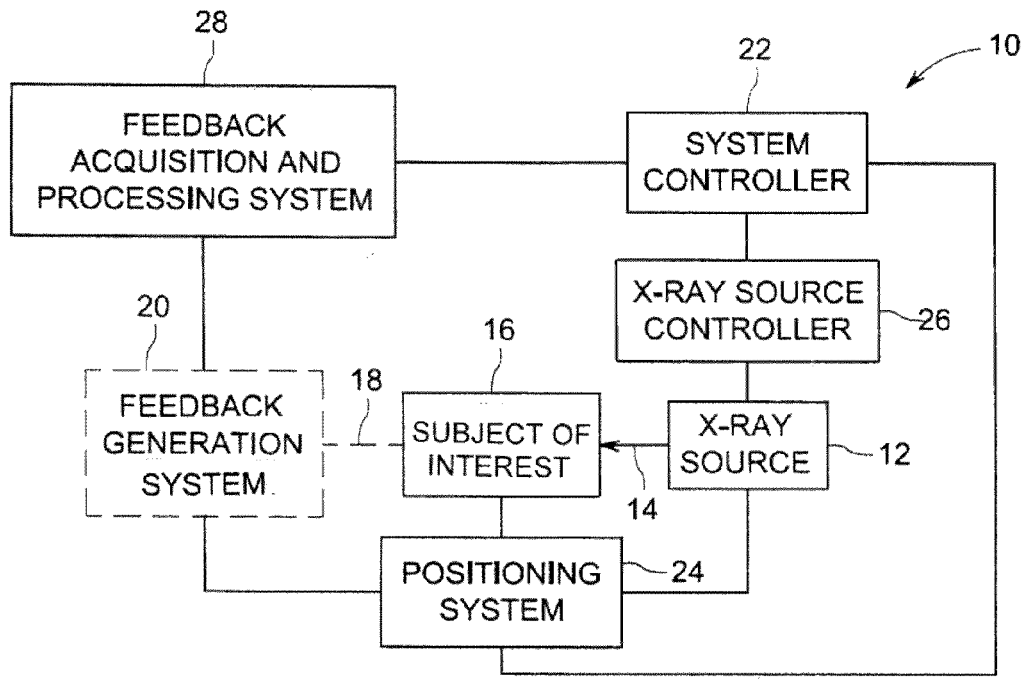
FIG. 1 is a block diagram illustrating an embodiment of a system that uses an X-ray source capable of emitting X-rays that may be used in conjunction with the dose estimation techniques according to an embodiment of the present disclosure.

While X-ray imaging and/or treatment devices may be configured to facilitate X-ray exposure at a sufficiently high dose to achieve desired results, operators may also wish to limit X-ray exposure for patients and/or X-ray technicians. The present disclosure provides X-ray dose estimation techniques that may be used to estimate X-ray doses of a patient (or exposed object) from particular settings used in conjunction with X-ray devices. As provided herein, the X-ray dose estimation approach may be prospective or retrospective and may be used to design and to assess dose-saving or dose-limiting features and protocols.

In contrast to Monte-Carlo simulation of photons, which is relatively slow and computationally expensive, the X-ray dose estimation as provided herein may be implemented at the point of service (e.g., just prior to an imaging scan). In particular, in Monte Carlo simulations, a range of plausible input values and a distribution is designated for each input variable, and a simulation generates random inputs for each input variable that are then used to calculate corresponding output values. This process is repeated, typically hundreds or thousands of times, to create statistically meaningful distributions of one or more of the output variables. Further, because Monte-Carlo photon simulation is typically performed retrospectively, appropriate baseline scan information may not be included with the assessed data, resulting in less accurate results. Accordingly, such techniques are not suited for accurate point-of-service X-ray dose estimation for a typical X-ray device that may serve many patients in a single day.

In certain embodiments, the X-ray dose estimation technique provided herein provides the benefit of projecting or estimating an X-ray dose prior to imaging or treatment. For example, the X-ray dose estimation may incorporate information from relatively lower X-ray dose preparatory scans (e.g., scout or reconstructed images from ultra-low dose acquisition scans) that occur before a full imaging scan. Such preparatory scans may involve a limited number of views or may involve multiple views of the patient. For example, information from a preparatory or scout scan may be used to determine an intensity profile for the scanned object. Based on the intensity profile of the detected X-rays and an estimate of the mass of the scanned object, a projected dose estimate may be determined. The dose estimate based on a preparatory scan may be further used (e.g., fitted to a line or used as a variable in a transfer function) in conjunction with the desired imaging or treatment energy settings to determine the projected dose to the object during imaging and/or treatment. In this manner, the estimated X-ray dose may be assessed on a per patient and per treatment basis. If the estimated dose is outside a desired range or threshold, the settings of the device may be changed, e.g., manually or automatically, until a desired estimated dose is achieved. In yet another embodiment, the dose estimation techniques may be used to retroactively determine the dose received by the scanned object. Such techniques may be useful for tracking or reporting total X-ray exposure of a patient or for tracking performance of a particular X-ray device.

Figure 2:
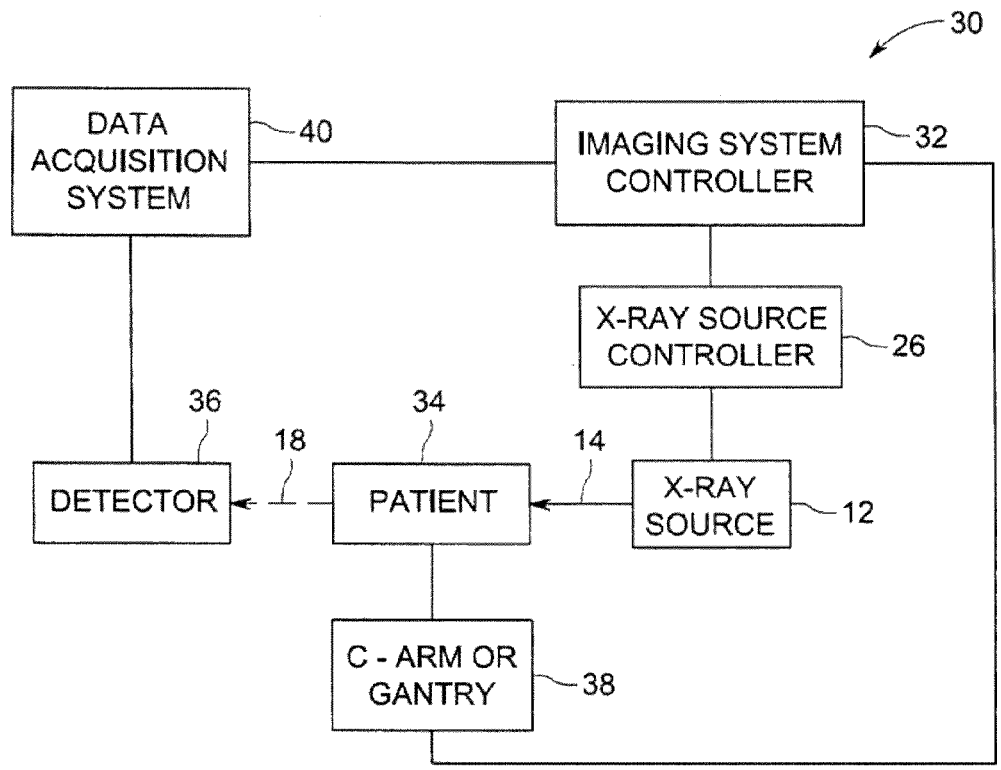
FIG. 2 is a block diagram illustrating an embodiment of an X-ray imaging system that uses an X-ray source capable of emitting X-rays that may be used in conjunction with the dose estimation techniques according to an embodiment of the present disclosure.

The approaches described herein may be used in the appropriate context, which may include non-invasive imaging, surgical navigation, radiation treatment, and so on. Accordingly, FIGS. 1 and 2 provide non-limiting examples of systems that may include control circuitry and control logic in accordance with the present approaches. Specifically, FIG. 1 is a block diagram illustrating a general system 10 that uses an X-ray radiation source 12 for performing a quality control, security, medical imaging, surgical, and/or treatment procedure. The X-ray radiation source 12 may include one or more X-ray tubes each having features for producing X-ray radiation from more than one perspective and/or of more than one energy in a controlled manner as noted above. The X-ray source 12 therefore produces one or more streams of X-ray radiation 14 that are directed towards a subject of interest 16. The subject of interest may be baggage, cargo, an article of manufacture, a tissue of interest, and/or a patient. The X-ray radiation 14 is directed towards the subject of interest 16, where the X-ray radiation is attenuated to produce a beam of attenuated X-rays 18. The beam of attenuated X-rays 18 is captured by a feedback generation system 20 to produce signals representative of an image, or other information that may be useful for performing the procedure. Again, the data produced at the feedback generation system 20 may include data produced from receiving X-rays from a variety of positions and/or energies from each X-ray tube of the source 12.

A system controller 22 commands operation of the system 10 to execute examination, treatment and/or calibration protocols and to process the feedback. With respect to the X-ray source 12, the system controller 22 furnishes power, focal spot location, focal spot size, control signals and so forth, for the X-ray examination sequences. For example, the system controller 22 may furnish focal spot sizes and/or locations for X-ray emissions by the X-ray source 12. Additionally, in some embodiments, the feedback generation system 20 is coupled to the system controller 22, which commands acquisition of the feedback. The system controller 22 may include signal processing circuitry and associated memory circuitry. In such embodiments, the memory circuitry may store programs, routines, and/or encoded algorithms executed by the system controller 22 to operate the system 10, including one or more features of the X-ray source 12, and to process the feedback acquired by the generation system 20. In one embodiment, the system controller 22 may be implemented as all or part of a processor-based system such as a general purpose or application-specific computer system.

The source 12 may be controlled by an X-ray source controller 26 contained within or otherwise connected to the system controller 22. The X-ray source controller 26 is configured to provide power and timing signals to the source 12. In some embodiments the X-ray source controller 26 may be configured to selectively activate the source 12 such that tubes or emitters at different locations within the system 10 may be operated in synchrony with one another or independent of one another. The X-ray source 12 is positioned about the subject of interest 16 by the positioning system 24. The positioning system 24, as illustrated, may be connected to the feedback generation system 20. The positioning system 24 may displace either or both of the X-ray source 12 and the feedback generation system 20 to allow the source 12 to image or treat the subject of interest 16 from a variety of positions. As an example, in a radiation treatment procedure, the positioning system 24 may substantially continuously displace the X-ray source 12 about the subject of interest 16, which may be a tissue of interest, while varying the energy of the X-ray radiation 14 emitted toward the tissue of interest. In this way, the tissue of interest is provided with a substantially continuous flux of X-ray radiation while X-ray exposure to outlying tissues is minimized.

Moreover, while some systems may not produce diagnostic images of the patient, the feedback generation system 20 may generate data relating to the position of the X-ray source 12 or other features, such as a surgical tool, relative to the tissue of interest, for example as an image and/or map. Such data may enable a clinician or other healthcare provider to ensure that the X-ray radiation 14 and/or the surgical tool is properly located with respect to the tissue of interest. The feedback generation system 20 may include a detector, such as a diode array, or a system that monitors the position of the source 12 and/or surgical tool relative to the subject of interest 16. Indeed, in certain embodiments, the feedback generation system 20 may include a detector and position-monitoring features that also provide feedback to the positioning system 24 either directly or indirectly.

To provide feedback to features of the system 10 that are not directly connected to or associated with the feedback generation system 20, the feedback generation system 20 provides data signals to a feedback acquisition and processing system 28. The feedback acquisition and processing system 28 may include circuitry for receiving feedback from the feedback generation system 20, as well as processing circuitry for manipulating the received data. For example, the processing circuitry may include signal converters (e.g., A/D converters), device drivers, processing chips, memory, and so on. In some embodiments, the feedback acquisition and processing system 28 converts analog signals received from the feedback generation system 20 into digital signals that can be further processed by one or more processing circuits (e.g., a computer-based processor) of the system controller 22.

One embodiment of system 10 is illustrated in FIG. 2, which is a block diagram of an embodiment of an X-ray imaging system 30, such as a computed tomography (CT) or other radiographic imaging system. The system 30 includes an imaging system controller 32 for acquiring and processing estimation data. The imaging system controller 32 also includes or is otherwise operatively connected to the X-ray source controller 26, which operates as described above. The X-ray source controller 26 may also be operatively connected to a plurality of magnetic coils that are disposed proximate an X-ray tube of the source 12.

Generally, the system 30 situates a patient 34 such that the X-ray beam 14 produced by the source 12 is attenuated by the patient 34 (e.g., various anatomies of interest) to produce the attenuated X-rays 18 that have passed through the patient 34, which may be received by a detector 36, such as a digital detector. In certain embodiments, the patient 34 may be situated in this manner using a patient table combined with a C-arm or gantry 38, which is controllably connected to the imaging system controller 32. Generally, the imaging system controller 32 may synchronize certain imaging sequence parameters, such as emissions from the source 12 with rotation rates of the source 12 and detector 36 about the gantry.

The data that is generated at the detector 36 upon receiving the attenuated X-rays 18 is provided, as above, to processing features such as the illustrated data acquisition system (DAS) 40. The DAS 40 generally converts the data received from the detector 36 into a signal that can be processed at the imaging system controller 32 (or other computer based processor). As an example, the detector 36 may generate analog data signals upon receiving the attenuated X-rays 18, and the DAS 40 may convert the analog data signals to digital data signals for processing at the imaging system controller 32. The data may be used to generate one or more volumetric images of various anatomies within the patient 34. Further, the data may be used to implement one or more embodiments of the disclosed techniques for X-ray dose estimation.

As noted, the above systems are examples of systems that may be used in conjunction with the X-ray dose estimation techniques disclosed herein. The methods may include various steps or actions represented by blocks in the flow diagrams herein. It should be noted that the methods may be performed as an automated procedure by a system, such as system 10 or system 30. Further, certain steps or portions of the method may be performed by separate devices or may involve operator actions or input.

Figure 3:
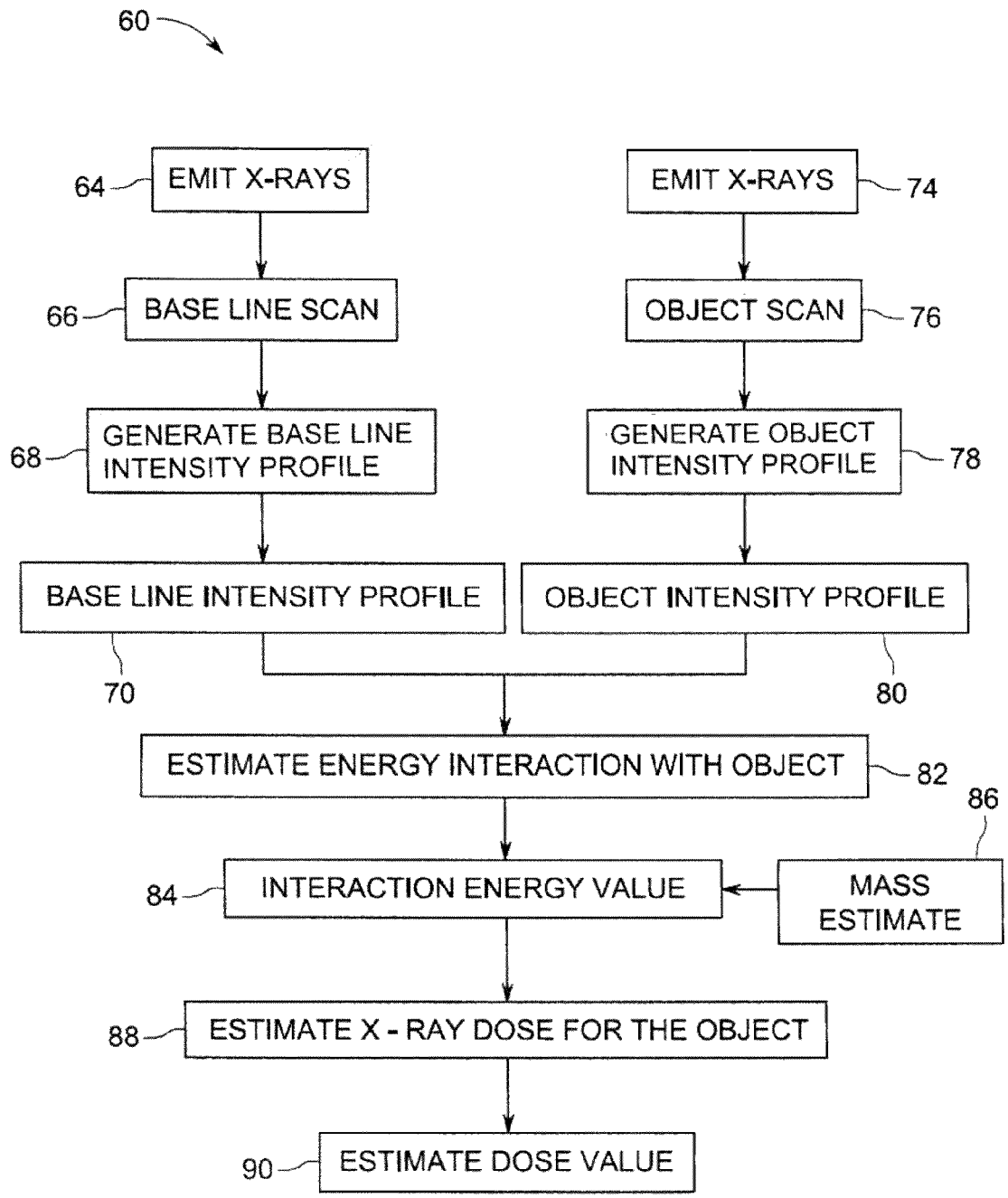
FIG. 3 is a flow diagram of a dose estimation technique according to an embodiment of the present disclosure.

FIG. 3 is a process flow diagram illustrating a method 60 of estimating an X-ray dose in accordance with some embodiments. According to the embodiment illustrated, the method 60 begins with emitting X-rays from an X-ray source 12 at block 64 to generate an air scan or baseline scan 66 at block 64. In one embodiment, the baseline scan 66 represents detection of X-rays when a scanned patient or object is not in the field of view (FOV). The baseline scanning step at block 64 may be performed periodically (e.g., prior to every dose estimation) or may be performed as a calibration step for the system (e.g., system 30) or the X-ray source 12 and the detector 36. For example, the calibration may be performed as part of the manufacturing process and the baseline scan results may be stored in a memory associated with the system 30 (e.g., a mass storage device associated with the DAS 40). The baseline scan results may include data from a detector that may be further processed and/or analyzed as provided herein. For example, the baseline scan is used (block 68) to generate a baseline intensity profile 70.

The patient or object of interest is scanned at block 74 to generate an object scan 76. The object scan 76 in turn may be used (block 78) to generate an object intensity profile 80. The intensity profiles 70 and 80 may be provided as raw data or may be provided as a plot of the energy over a range of channels or positions. For example, the intensity may be expressed in any appropriate absolute intensity unit or as an arbitrary relative unit. Further, the intensity may be expressed with regard to position of the scanned object. The position may be expressed as a measured position within the field of view, a distance from a center of the field of view, a pixel position, or as a position associated with a particular channel. The baseline intensity profile 70 and the object intensity profile 80 are used to estimate the energy interaction with the object (block 82) to generate an interaction energy value 84. The interaction energy value 84 and a mass or size estimate 86 for the object are used to estimate an X-ray dose (block 88) to generate an estimated dose value 89 for a particular X-ray setting.

The estimated dose value 89 may in turn be displayed or otherwise provided as an indication to an operator of an associated system (e.g., system 10 or system 30) The estimated dose value 89 may be compared manually or automatically to a range or threshold to determine if the estimated dose value 89 is appropriate for the desired application. Further, the estimated dose value 89 may be used to automatically select settings for the associated system, including imaging or treatment settings.

Figure 4:
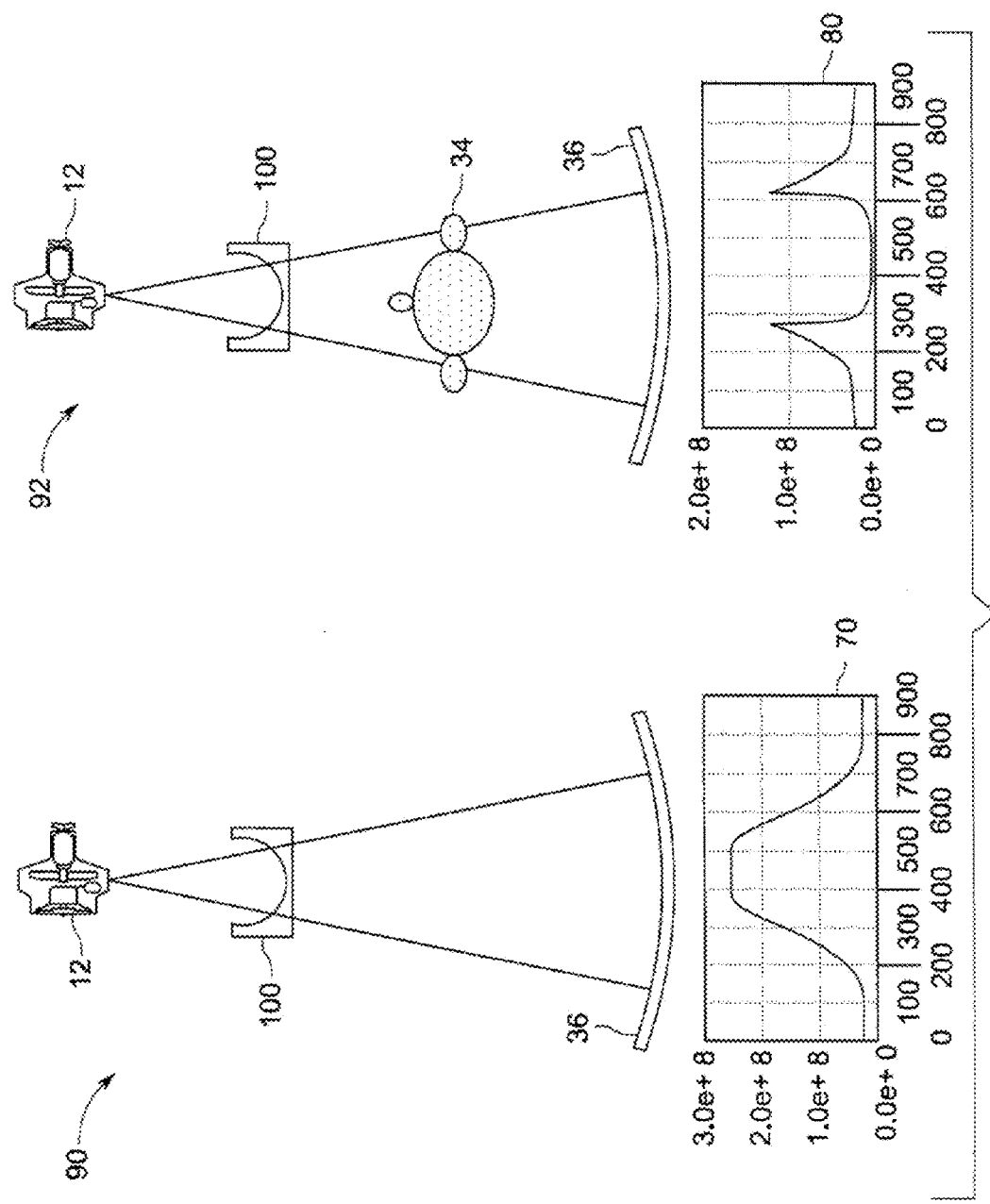
FIG. 4 is a schematic view of an embodiment of an X-ray system in a baseline scan mode and an object scan mode that may be used in conjunction with the dose estimation techniques according to an embodiment of the present disclosure.

For example, the intensity profiles 70 and 80 generated by a patient and object scan, respectively, are shown in FIG. 4, which shows side-by-side schematic views of an example of a baseline scan 90 and an object scan 92. After photons from an X-ray tube first pass through beam shaper 100, which may include components such as a bowtie filter, collimator, and so forth, they are absorbed, scattered by, or pass through the object, shown as patient 34. The photons that do not get absorbed are detected at the detector 36. In the baseline scan case, most of the photons pass through to the detector 36. With the exception of any scattered photons, the lost intensity energy in the object scan is through energy absorption by the object or the energy interaction with the object. The difference between the baseline intensity profile 70 and the object intensity profile 80 represents the lost intensity due to the patient 34 and, thus, may be translated into the energy absorbed by the patient 34.

Figure 5:
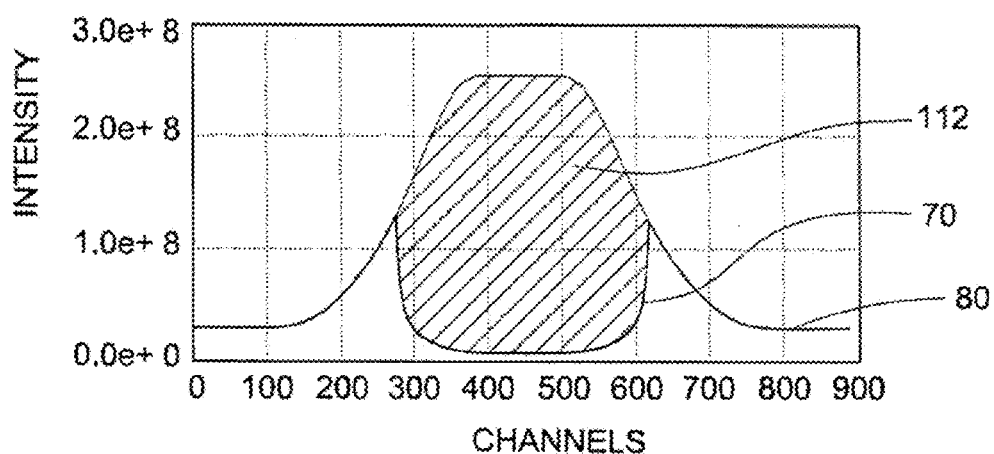
FIG. 5 is an example of a combined baseline intensity profile and object intensity profile that may be used to estimate an interaction energy in conjunction with the dose estimation techniques according to an embodiment of the present disclosure.

The baseline intensity profile 70 and the object intensity profile 80 may be used in conjunction with one another to determine an energy interaction with the object or patient 34. As shown in FIG. 5, an example of a combined plot 110 shows a shaded area 112 between the baseline intensity profile 70 and the object intensity profile 80 when aligned along the x-axis 120 and where the y-axis represents a common relative intensity scale. Here, the shaded area between the two curves represents an estimate of the energy interaction with the object or patient 34. In certain embodiments, the baseline scan 66 and the object scan 76 may include data from a single view (i.e., only one view) or may involve multiple views. Fewer views may be associated with relatively faster analysis. That is, the X-ray source 12 and patient 34 may move relative to one another so that multiple images may be acquired, such as at different radial views. In such embodiments, the estimates of interaction energy determined via intensity profiles 70 and 80 from individual views may be combined or averaged. In other embodiments, an estimated dose may be determined on a per view basis.

Figure 6:
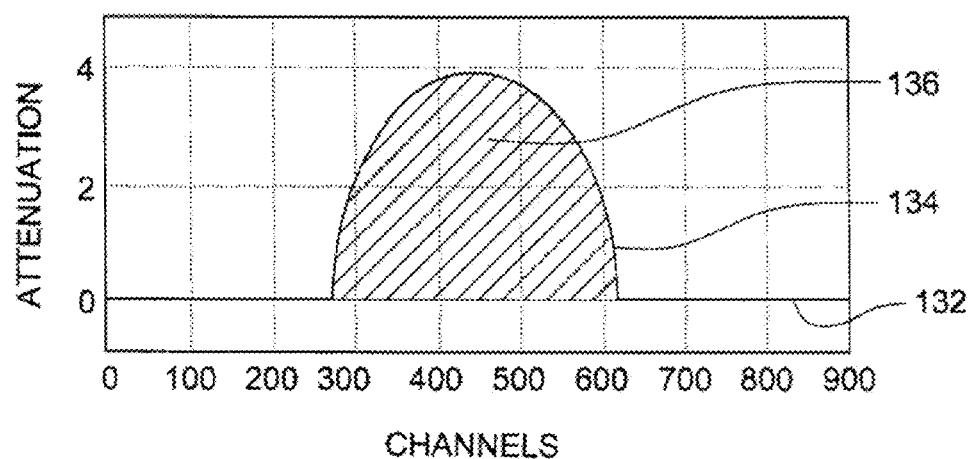
FIG. 6 is an attenuation profile that may be used to estimate object mass in conjunction with the dose estimation techniques according to an embodiment of the present disclosure.

In addition to determining an energy interaction with the object, the data from the detector 36 may also be used to estimate the object's mass. FIG. 6 is an example of a combined attenuation profile 130 generated from the preparation routines using calibration scans and an object scan. Since heavy (i.e., denser) materials generally yield high attenuation and light (i.e., less dense) materials generally yield low attenuation, the shaded area 136 under attenuation profile may be be used as the substitute to the mass of object. However, as discussed herein, the mass may be estimated through one or more other techniques, such as those provided herein. By using these two substitutes or estimates for interaction energy and mass, the dose per given view may be computed as:

$$DE_j = \frac{E_j}{m_j}, \quad (1)$$

where $DE_j$ represents the dose estimation at view j, $E_j$ represents the interaction energy at view j or area between air and object scan intensity curves, shown in FIG. 4(a), and $m_j$ represents the mass contribution at view j or area below attenuation curve. $DE_j$ can be used as a rough dose metric per view since it can be computed relatively easily on the fly. Furthermore, aggregated dose metric per image slice may be also defined as $$DE = \sum_j \frac{E_j}{m_j}, \quad (2)$$

where DE represent the dose estimation of the image slice corresponding to the detector row. This metric represents the dose per illuminated local region. Further, the whole body dose metric may be computed by either using real weight of the patient or using factors associated with the percentage of exposed body volume and the dose sensitivity of illuminated volume.

$$DE_{whole\ body} = \frac{\Sigma_j E_j}{\text{Patient weight}}, \quad (3)$$

or $$DE_{whole\ body} = \sum \% \text{ of exposed volume} \cdot \text{dose sensitivity} \cdot DE_{local}, \quad (4)$$

In cases in which the X-ray beam has a cone geometry, this approximation may be corrected to accommodate multiple row contribution to the image slices located off from iso plane.

Figure 7:
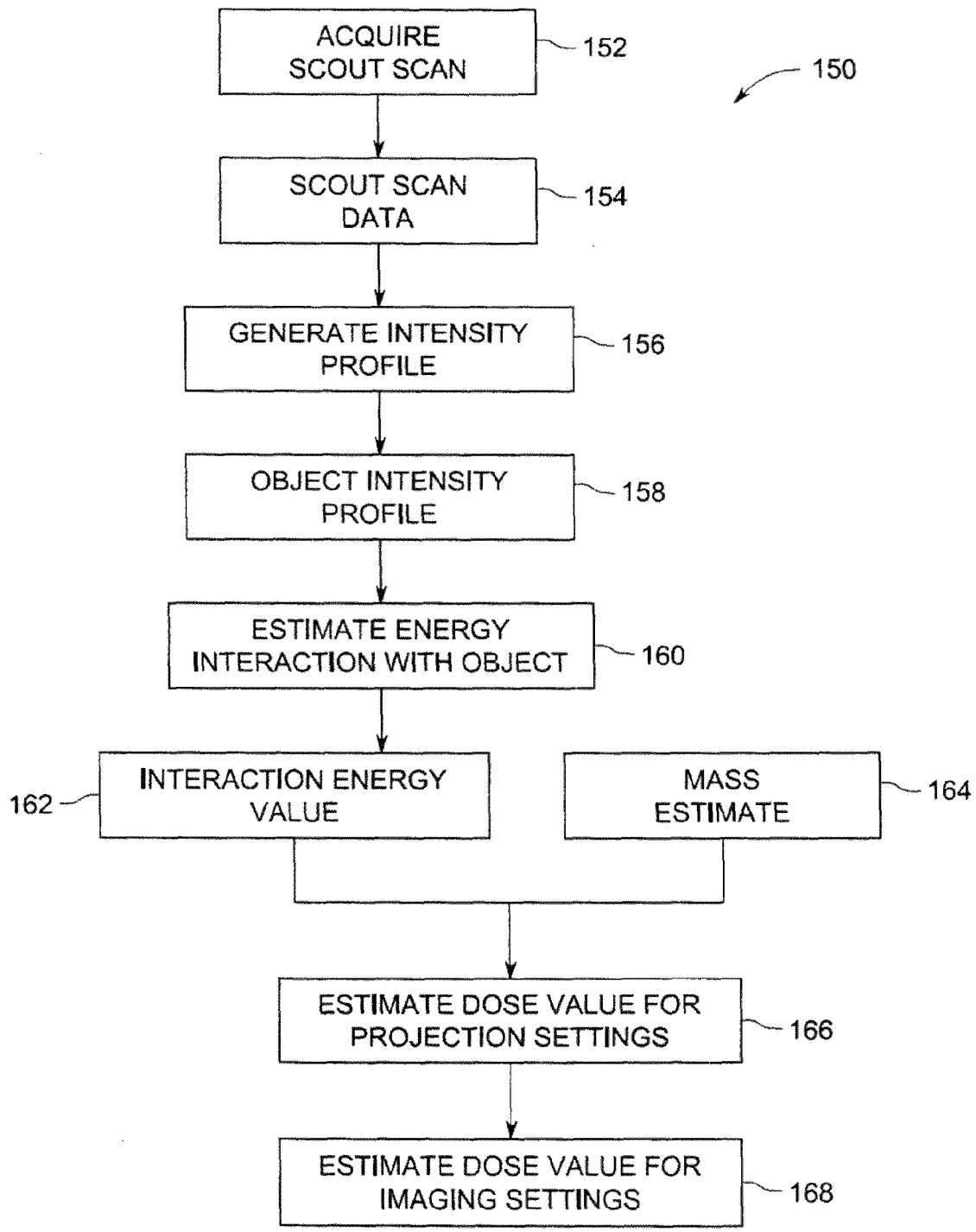
FIG. 7 is a flow diagram of an imaging dose estimation technique according to an embodiment of the present disclosure.

The disclosed X-ray dose estimation implementations may be used to estimate a CT imaging dose, as illustrated in the flow diagram of FIG. 7. The method 150 begins with acquiring a preparatory or scout image of a patient at scout settings for the CT device at block 152 to obtain scout image data 154. An object intensity profile (158) of the scout image data is generated (block 156). Based on the object intensity profile, the method 150 estimates the interaction energy in the patient at block 160 to acquire an interaction energy value 162. The method 150 acquires a mass estimate at block 164, either from the scout image data 154 (as shown) or other source, and determines an estimated dose at the scout settings at block 166 to output an estimated dose value 168. To determine an estimated dose at the imaging settings at block 170, the estimated dose value 168 at the scout settings are used to extrapolate an estimated dose value at the imaging settings. For example, the data may be fitted to a line or used as variables in a transfer function that is solved for the imaging settings in question. In other embodiments, the scout image data 154 and/or the estimated dose value 168 may be matched to a closest set of modeled or empirical data (e.g., based on imaged phantoms) to estimate the imaging dose. In a specific embodiment, the empirical data may be corroborated to Monte-Carlo based results to estimate estimated imaging doses.

The estimated dose value 168 at the imaging settings may be compared to an acceptable range or threshold, either manually or automatically. A value outside of an acceptable range or threshold may trigger an alarm or may be used to exclude certain imaging settings from consideration. For example, the method 150 may be incorporated into an automatic dose-selecting feature for an X-ray device. In one embodiment, the imaging settings may be selected so that the estimated dose value 168 is within a desired range or may be optimized to a lowest possible value. In certain embodiments, the estimated dose value may be provided as an output to an operator or caregiver. For example, the estimated dose value for an imaging run may be bundled with the imaging data provided to the caregiver.

The dose estimation techniques disclosed herein, because they are relatively faster than Monte Carlo-based strategies, provide the benefit of dose estimation for each patient at the time the image is acquired, i.e., the dose estimation and image acquisition may occur in a single imaging appointment for the patient. Such individualized dose estimation provides more accurate dose estimation for patients that are different sizes and have different anatomies. Further, each patient may be imaged in different areas of the body. Because different organs have different X-ray absorption profiles, doses for imaging may be determined not only on a per-patient basis, but for individual organs in the desired imaging field. Further, in certain embodiments, the dose estimation techniques may be performed without any corroboration from Monte-Carlo based strategies. That is, the dose estimation techniques may replace Monte-Carlo analysis.

EXAMPLES

Figure 8:
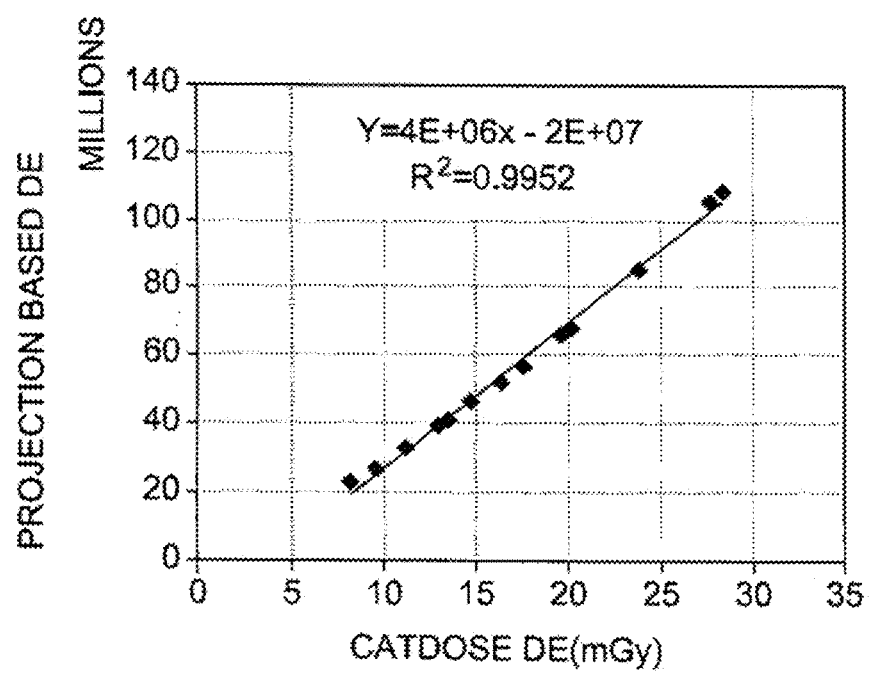
FIG. 8 is a plot of projection-based dose estimates versus Monte-Carlo based estimates for 8 cylindrical water phantoms and 7 ellipsoidal water phantoms where the cylindrical phantom sizes vary from 12 cm to 40 cm in diameter and ellipsoidal phantom sizes vary from 16 cm by 100 mm to 400 mm by 260 mm.

The following examples represent imaging simulations used to determine a relationship between dose metrics and actual average dose per irradiated slice or volume. In particular, 8 cylindrical phantoms and 7 ellipsoidal phantoms made out of water and with various sizes were modeled. Phantoms were simulated in both Catsim (GE Global Research Center, Niskayuna, N.Y.) to compute projection-based dose metrics and Catdose (GE Global Research Center, Niskayuna, N.Y.) to compute average dose per image slice using a Monte-Carlo strategy. Cylindrical phantom sizes vary from 120 mm to 400 mm in diameter and ellipsoidal phantom sizes vary from 160 mm by 100 mm to 400 mm by 260 mm. Average dose per image slice was computed by averaging all the pixels of object in dose map. Estimation-based dose metrics and average doses per image slice from Monte-Carlo simulation are shown in FIG. 8. The plot includes a linear regression result with a correlation $R^2$ of 0.9952.

Figure 9A:
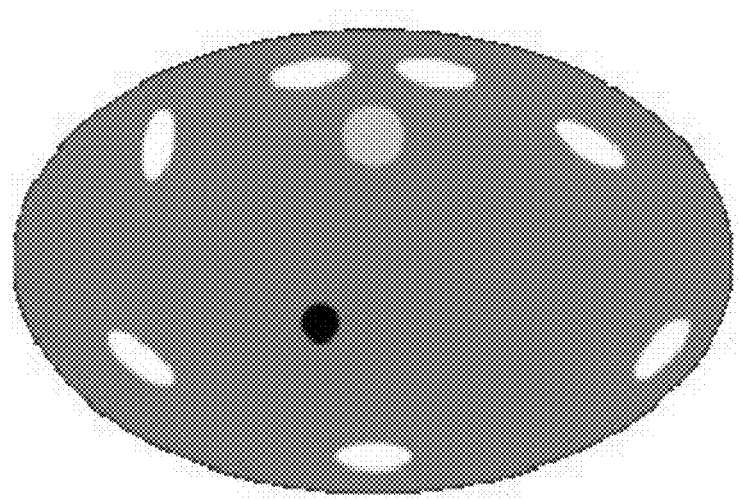
FIG. 9A is a view of a helical body phantom.

Helical body phantoms (HBPs) representing an abdomen area included a water-filled ellipsoid, several small ellipsoids for ribs, and two circular areas for spine and air bubbleviews of which are shown in FIG. 9A. The HBPs modeled anatomies with different materials.

Figure 9B:
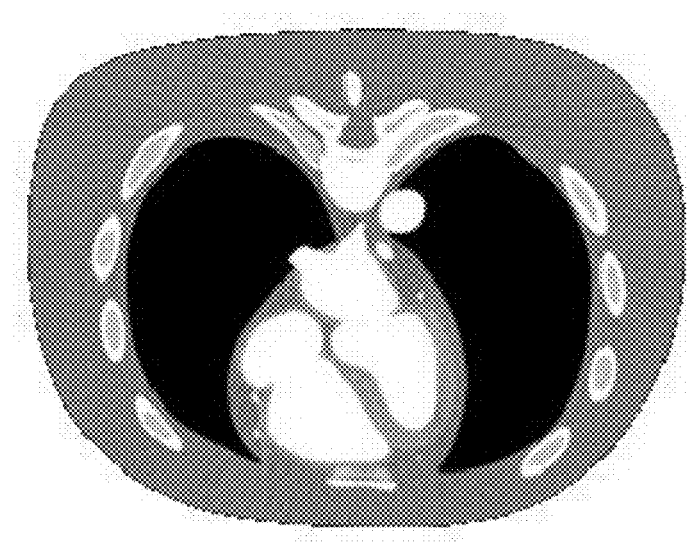
FIG. 9B is a view of a transverse plane of a 4D NURBS-based Cardiac-Torso (NCAT) phantom.
Figure 10:
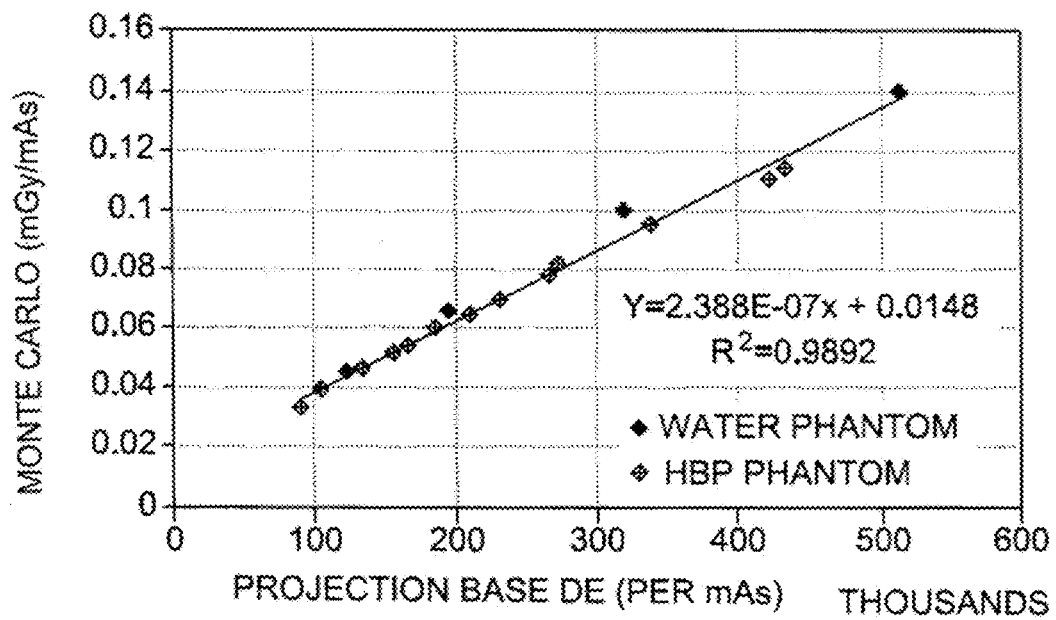
FIG. 10 is a plot of projection-based dose estimates versus Monte-Carlo based estimates showing correlation with 15 water phantoms with various sizes as in FIG. 8 and helical body phantoms ranging from 10 cm by 7.5 cm to 40 cm by 26 cm.
Figure 11:
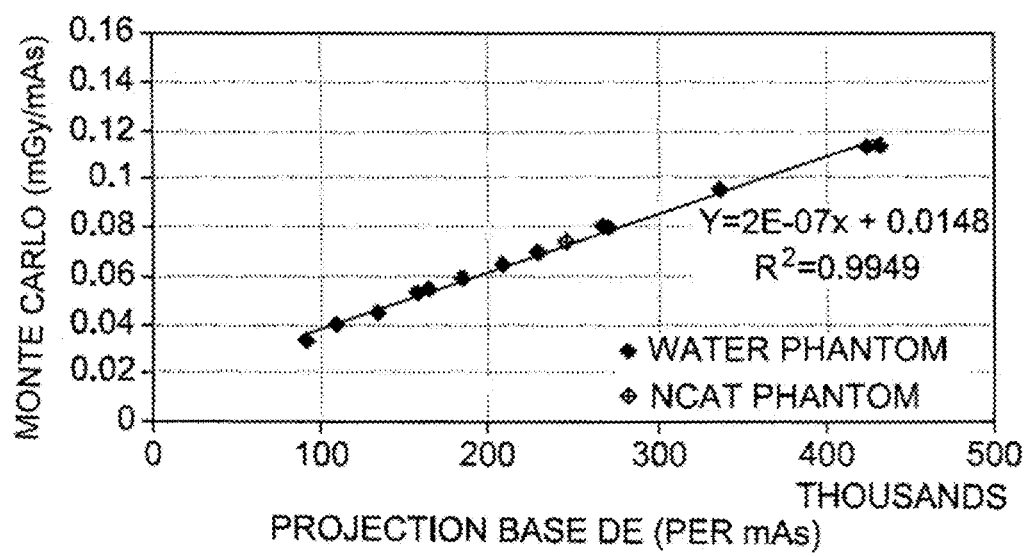
FIG. 11 is a plot of projection-based dose estimates versus Monte-Carlo based estimates showing correlation with 15 water phantoms as in FIG. 8 and an nCat phantom.

Various sizes of HBPs were simulated both in Catsim and Catdose to determine actual average dose and estimation-based dose estimates. Furthermore, the chest of nCAT phantom, numerically generated anthropomorphic phantom shown in FIG. 9B, was also simulated. Estimation-based dose metrics and average doses per image slice are shown in FIG. 10 and FIG. 11. In particular, a slight concavity in the associated HBP cases was observed in FIG. 11. This may indicate that the correlation is nonlinear.

Figure 12:
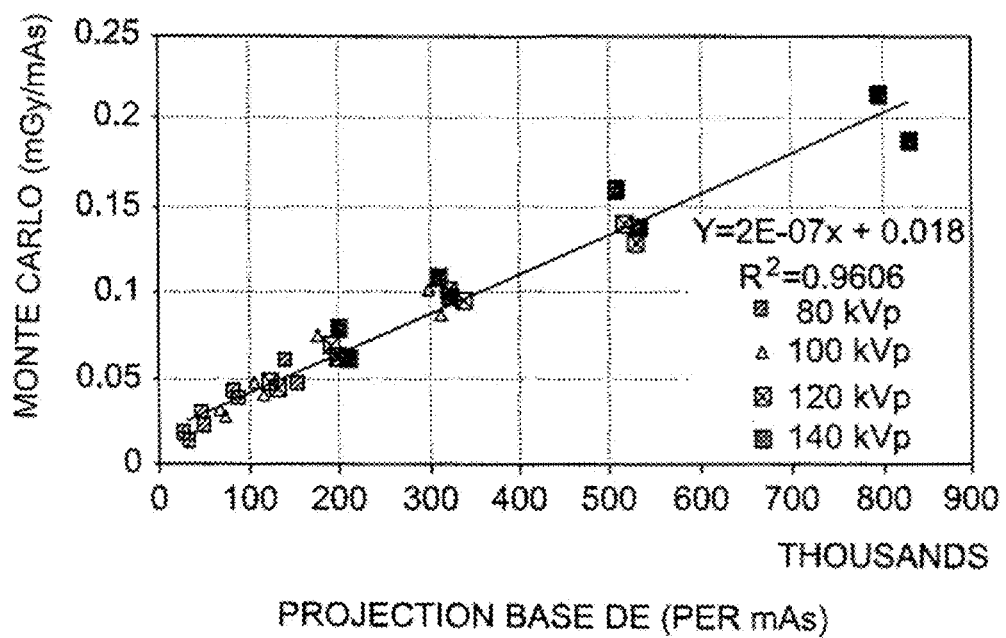
FIG. 12 is a plot of projection-based dose estimates versus Monte-Carlo based estimates over a range of kVp doses.

Furthermore, HBPs and corresponding sizes of water phantom were simulated with kVp ranging from 80 kVp to 140 kVP. Estimation-based dose metrics and average doses per image slice are shown in FIG. 12. Since dose may drop by a factor of 4 when kVp is reduced from 140 kVp to 80 kVp, in particular embodiments, dose metrics may be normalized over kVp to improve correlation between estimation-based dose metric and Monte-Carlo based dose estimates.

Figure 13:
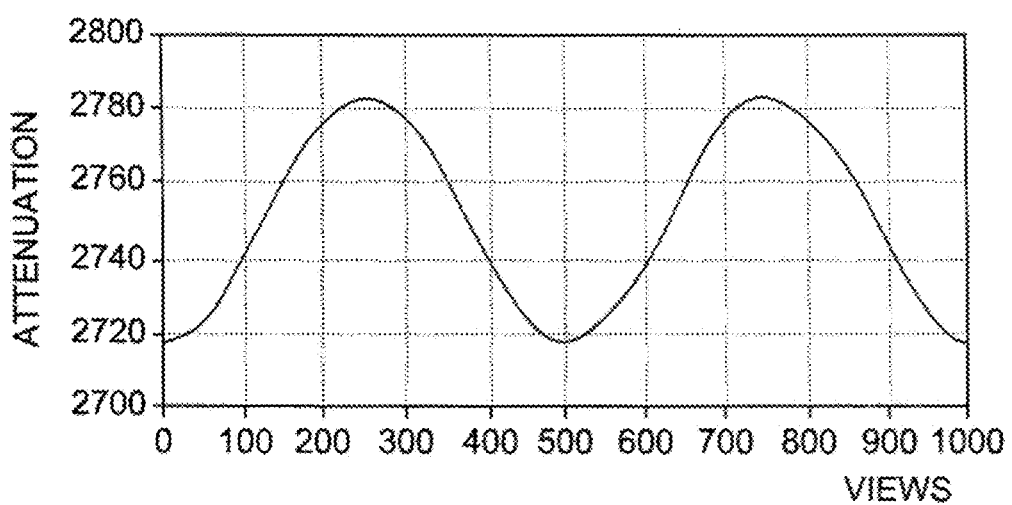
FIG. 13 is a plot of projection-based dose estimates versus Monte-Carlo based estimates over a range of kVp settings of system.

While certain embodiments may use a mass estimation via computing the area under attenuation curve, this may result in the fluctuation among views of mass estimates. In the modeled water ellipsoid phantom, mass estimates followed sinusoidal curve, shown in FIG. 13. In the actual case, mass does not change over views. Therefore, instead of using per-view mass substitute to determine an estimated dose, the average mass over multiple view may be used according to the equation:

$$DE = \frac{\Sigma_j E_j}{\frac{\Sigma_j m_j}{\# \text{ number of views}}}, \quad (5)$$

Figure 14:
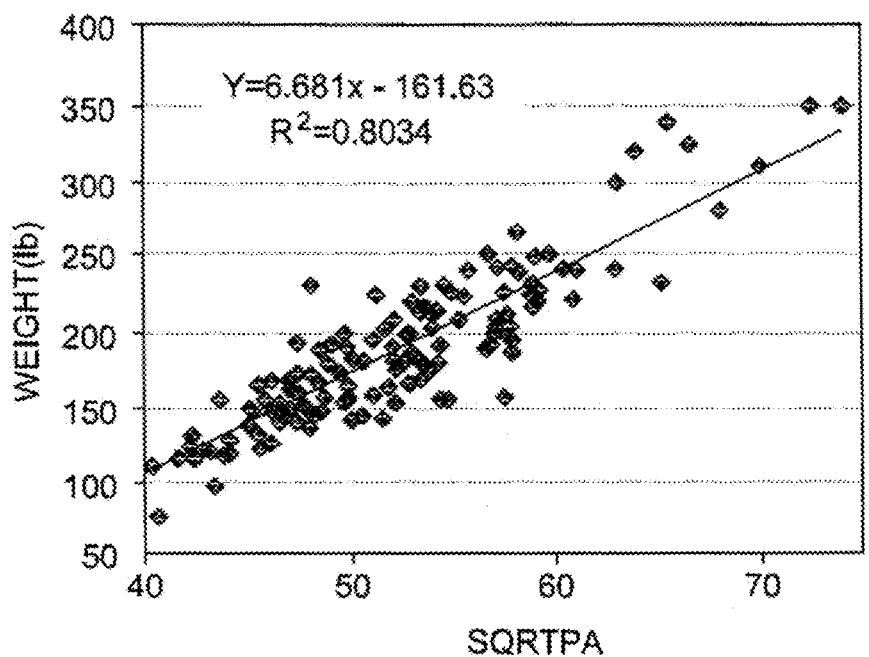
FIG. 14 is a plot of patient weight versus a patient attenuation indicator.
Figure 15:
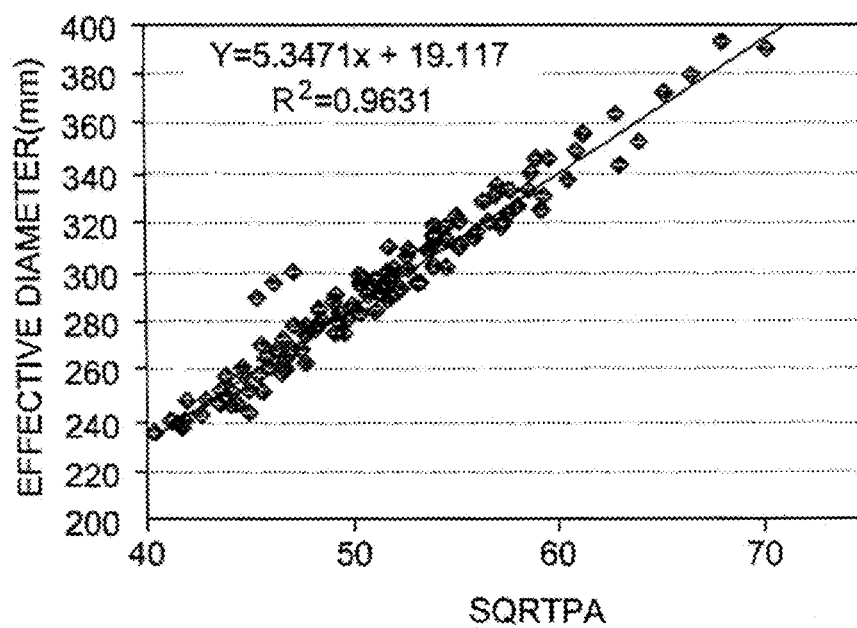
FIG. 15 is a plot of estimated effective diameter versus a patient attenuation indicator.

Furthermore, other mass substitutes may be used. For example, a patient attenuation indicator (PAI) shows strong correlation with the weight of patient (FIG. 14) and a correlation with the effective diameter of patient, as shown in the plot of FIG. 15. The patient attenuation indicator may be determined by taking square root of area under attenuation profile and subsequently multiplying by scaling factor of 0.557. Accordingly, in certain embodiments of the present disclosure, the mass estimate used in an estimated dose may be a patient attenuation indicator.

Figure 16:
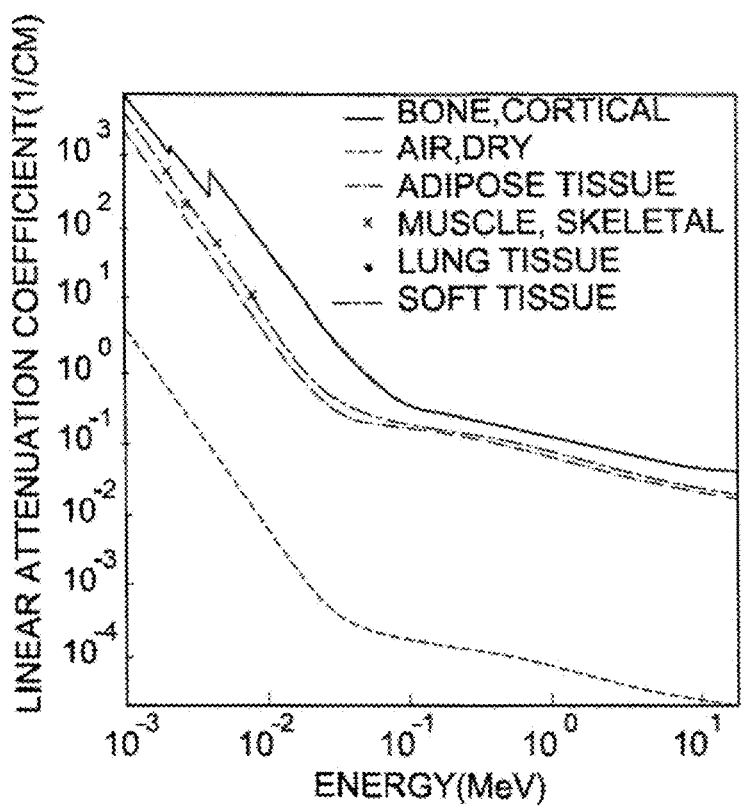
FIG. 16 is a plot of linear attenuation coefficient of anatomical materials.

An attenuation coefficient may also be used as an indicator of material density, assuming that generally denser materials yield high attenuation and less dense materials yield low attenuation. A mass correction factor might be added to better correlate such relationships and according to anatomical structures that are imaged. The ratio of projection-based density estimation between different materials may incorporate the density as ground truth. FIG. 16 shows the linear attenuation coefficient of different materials of the human body. The mass substitute in projection base, $\mu_{effective}(E)$, may be estimated as a weighted sum $\mu(E)$ of across spectrum energy bins. Since bone and soft tissue generally represent the range of density of materials that are found in the human body, the ratio between true density of soft tissue and bone may serve as a correction factor for the mass substitute $\mu_{effective}(E)$ in the projection base. Accordingly, in certain embodiments of the present disclosure, the mass estimate may account for different densities of materials by using such a correction factor.

Figure 17:
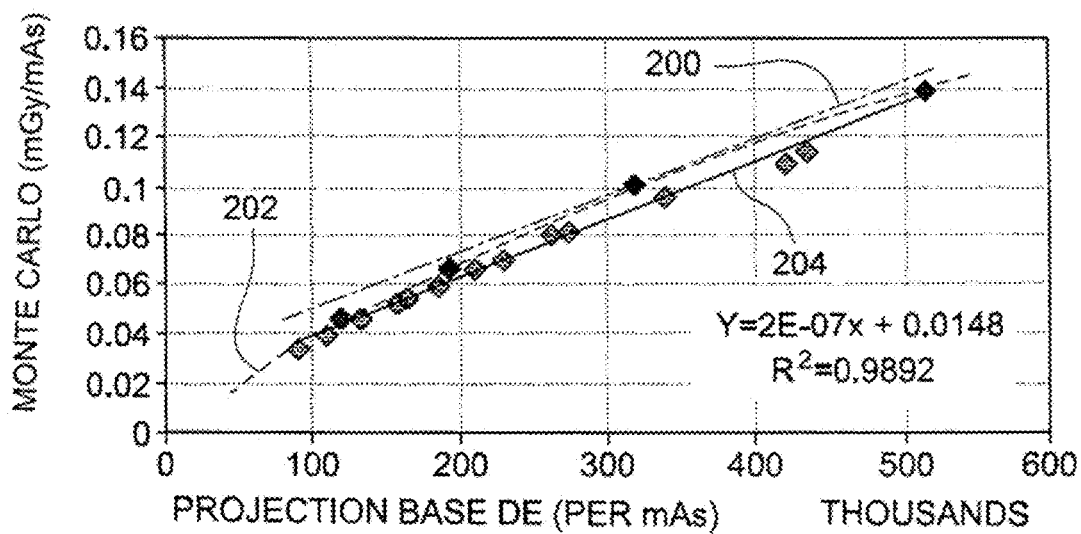
FIG. 17 is a plot of projection-based dose estimates versus Monte-Carlo based estimates showing correlation for helical body phantoms showing a scatter effect.

Further, in particular embodiments, the estimated dose of the object may account for photon scatter. The scatter effect may be patient size-dependent, energy dependent and/or material dependent. For example, a larger patient may have larger surface area so that more photons may escape. On the other hand, smaller patients may have shorter path length so that more photons may escape. Therefore, a estimation-based approach for either very small or very large patients may overestimate the dose compared to more average-sized patient. FIG. 17 show results from various sizes of HBP and water phantoms that may show such discrepancies. Compared to the line 200, which represents line passing middle-size phantom result and parallel to linear trend line 204, the projection-based approach overestimates for the larger and small sizes, i.e. to fit results from whole range of sizes, line 204 should be adjusted. Such adjustment may take place via an appropriate adjustment factor or transfer function. The size-dependent scatter effect can be computed by using Monte-Carlo scatter simulation a priori and correction factors may be applied to the projection-based dose estimates. On the other hand, the concave trend curve, similar to 202, where size-dependent scatter effect is already considered, may be used instead of the straight trend line.

Since Catsim simulations only account for primary signal at the detector, the scatter effect is considered negligible in certain embodiments of the projection-based dose metric. On the other hand, Monte-Carlo based dose estimation tracks individual photons and takes scatter into account when it computes absorbed energy. However, in embodiments in which the projection-based dose estimation assumes that all the scattered photons are reabsorbed, the interaction energy computed from estimations will be always larger than actual absorbed energy, and the resulting projection-based dose estimates may tend to overestimate the dose.

The acquired detector signal represents intensity after scintillator absorption, not incoming intensity. This scintillator-photon interaction, represented as quantum detection efficiency (QDE), may be corrected to yield the incoming intensity, which may improve the correlation between projection-based dose estimates and Monte-Carlo based dose estimates. QDE is defined by $$QDE(E) = e^{-\Sigma_i \mu_i(E) \cdot l_i}(1 - e^{\mu_{det}(E) \cdot l_{det}}), \quad (6)$$

$$I_t^{after\ absorption}(E) = QDE(E) \cdot I_t^{incoming}(E), \quad (7)$$

where t=1, 2, ..., T refer to the various pre-detector filter materials, and $\mu_{det}(E) \cdot l_{det}$ is the attenuation term of the detector scintillator (e.g. CsI). With known scintillator and filter material and length, an energy-dependent detector response can be removed to yield higher correlation between projection-based dose estimation and Monte-Carlo based dose estimation. Accordingly, in certain embodiments of the disclosed technique, the estimated dose may be corrected for photon scatter effects.

This written description uses examples to disclose certain embodiments of the disclosure, including the best mode, and also to enable any person skilled in the art to practice the disclosed implementations, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray system comprising:
   an X-ray source configured to generate an X-ray beam;
   a detector configured to detect X-rays of the X-ray beam that pass through an object, and to detect X-rays of the X-ray beam when the object is not in a field of view; and
   a processor coupled to the detector and configured to receive information generated by the detector related to the detected X-rays, and wherein the processor is configured to execute instructions for:
   determining an object intensity profile from the object scan of the detected X-rays that pass through the object and determining a baseline intensity profile using a baseline scan of the detected X-rays when the object is not in view;
   determining a combined attenuation profile of the detected X-rays that pass through the object, wherein the combined attenuation profile is generated by combining the object scan and the baseline scan;
   estimating an energy interaction with the object based on the baseline intensity profile and the object intensity profile;
   estimating a mass of the object based on the combined attenuation profile; and
   determining an estimated dose value based at least in part on the energy interaction with the object and the mass of the object.

2. The X-ray system of claim 1, wherein the estimated dose value comprises $$DE_j = \frac{E_j}{m_j},$$

where $DE_j$ is the estimated dose value, $E_j$ is the estimated interaction energy, and $m_j$ represents the estimated mass.

3. The X-ray system of claim 1, wherein estimating an energy interaction with the object based on the intensity profile comprises determining an area between a baseline X-ray intensity profile without the object and the intensity profile of the detected X-rays that pass through the object.

4. The X-ray system of claim 1, wherein the information from the detector related to the detected X-rays comprises information from a plurality of views.

5. The X-ray system of claim 4, wherein the estimated dose value comprises a sum of estimated dose values from the plurality of views.

6. The X-ray system of claim 4, wherein the estimated dose value is determined using the equation $$DE_{whole\ body} = \frac{\Sigma_j E_j}{\text{Patient weight}},$$

where $DE_j$ is the estimated dose value and $E_j$ is the estimated interaction energy for the plurality of views.

7. The X-ray system of claim 1, wherein the intensity profile comprises an intensity of detected X-rays over a range of positions.

8. The X-ray system of claim 1, wherein the attenuation profile comprises attenuation of energy of detected X-rays over a range of positions.

9. The X-ray system of claim 1, comprising estimating an imaging dose for an imaging scan of the object based on the estimated dose value.

10. The X-ray system of claim 9, wherein estimating the imaging dose for the object comprises using the estimated dose value and an imaging energy as variables in a transfer function.

11. A method, comprising:
    providing an X-ray source configured to generate an X-ray beam;
    providing an X-ray detector configured to detect X-rays of the X-ray beam that pass through an object, and to detect X-rays of the X-ray beam when the object is not in view;
    using a processor:
    receiving information using an object scan generated by the X-ray detector related to one or more X-ray images of an object;
    determining an object intensity profile using the object scan of detected X-rays that pass through the object based on the information;
    determining a baseline intensity profile of the detected X-rays using a baseline scan when the object is not in view;
    determining a combined attenuation profile of detected X-rays based on the information, wherein the combined attenuation profile is generated by combining the object scan and the baseline scan;
    estimating an energy interaction with the object based on the intensity profile;
    estimating a mass of the object based on the combined attenuation profile; and
    determining an estimated dose value based at least in part on the energy interaction with the object and the mass of the object.

12. The method of claim 11, comprising determining an X-ray imaging energy for the object based on the estimated dose value.

13. The method of claim 11, comprising providing an indication of the X-ray imaging energy on a display.

14. The method of claim 11, wherein estimating the mass comprises estimating an average mass from a plurality of X-ray images.

15. The method of claim 11, wherein estimating the mass comprises correcting an estimated mass based on a correction factor.

16. The method of claim 11, wherein determining an estimated dose value comprises correcting for photon scattering.

17. An X-ray system, comprising:
an X-ray source configured to generate an X-ray beam;
an X-ray detector configured to detect X-rays of the X-ray beam that pass through an object, and to detect X-rays of the X-ray beam when the object is not in view;
a processor configured to receive information generated by an X-ray detector related to X-rays that have passed through an object, wherein the processor is configured to execute instructions for:
  determining an object intensity profile from the object scan of the detected X-rays that pass through the object;
  determining a baseline intensity profile using a baseline scan of the detected X-rays when the object is not in view;
  estimating an energy interaction with the object based on the object intensity profile and the baseline intensity profile; and
  determining an estimated dose value based at least in part on the energy interaction with the object and an estimated mass of the object.

18. The X-ray system of claim 17, wherein the estimated mass comprises an average mass determined based on a combined attenuation profile of a plurality of X-ray images; wherein the combined attenuation profile is generated by combining one or more object scan and the baseline scan.

19. The X-ray system of claim 17, wherein the estimated dose value is reduced to account for a photon scatter effect.

20. The X-ray system of claim 17, wherein the estimated mass is corrected to account for a density of the object.

21. The X-ray system of claim 17, wherein the processor is configured to execute instructions for projecting an imaging dose based on the estimated dose value and one or more imaging settings.

22. The X-ray system of claim 21, wherein the processor is configured to provide an indication related to the imaging dose to an operator.

* * * * *